United States Patent
Tsujii

(10) Patent No.: US 9,031,190 B2
(45) Date of Patent: May 12, 2015

(54) X-RAY IMAGING APPARATUS

(75) Inventor: Osamu Tsujii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 405 days.

(21) Appl. No.: 13/528,975

(22) Filed: Jun. 21, 2012

(65) Prior Publication Data

US 2013/0003927 A1    Jan. 3, 2013

(30) Foreign Application Priority Data

Jun. 29, 2011  (JP) ................. 2011-144550

(51) Int. Cl.
| | |
|---|---|
| G01N 23/083 | (2006.01) |
| H05G 1/46 | (2006.01) |
| H05G 1/44 | (2006.01) |
| H05G 1/30 | (2006.01) |
| A61B 6/00 | (2006.01) |
| A61B 6/04 | (2006.01) |

(52) U.S. Cl.
CPC .......... *A61B 6/4452* (2013.01); *G01N 2223/32* (2013.01); *A61B 6/0407* (2013.01); *A61B 6/4458* (2013.01); *A61B 6/461* (2013.01); *A61B 6/486* (2013.01); *A61B 6/488* (2013.01); *A61B 6/503* (2013.01); *A61B 6/587* (2013.01)

(58) Field of Classification Search
CPC .... A61B 6/4452; A61B 6/4458; A61B 6/486; A61B 6/587; A61B 6/0407; A61B 6/461; A61B 6/488; A61B 6/503; G01N 2223/32
USPC ............ 378/51, 56, 62, 91, 95–98, 98.8, 101, 378/106, 108, 114–117, 162, 165, 193, 197, 378/198, 204, 205, 207, 210
See application file for complete search history.

(56) References Cited

U.S. PATENT DOCUMENTS

| | | | |
|---|---|---|---|
| 6,185,274 B1 | 2/2001 | Kinno et al. ................. 378/98.8 |
| 6,583,420 B1 * | 6/2003 | Nelson et al. ................. 250/397 |
| 7,050,537 B2 | 5/2006 | Tsujii ............... 378/95 |
| 7,315,606 B2 | 1/2008 | Tsujii ............... 378/20 |
| 7,564,998 B2 | 7/2009 | Tsujii ............... 382/128 |
| 8,131,050 B2 | 3/2012 | Tamai et al. .................. 382/132 |
| 2004/0086204 A1 | 5/2004 | Shoji ............. 382/312 |
| 2007/0025500 A1 * | 2/2007 | Horiuchi et al. ............... 378/16 |
| 2007/0253534 A1 * | 11/2007 | Abe ............... 378/116 |
| 2009/0122952 A1 * | 5/2009 | Nishide et al. ............... 378/4 |
| 2009/0285468 A1 * | 11/2009 | Omi ............. 382/132 |

(Continued)

FOREIGN PATENT DOCUMENTS

| | | |
|---|---|---|
| JP | 11-331703 | 11/1999 |
| JP | 2000-292598 | 10/2000 |

(Continued)

*Primary Examiner* — Anastasia Midkiff
(74) *Attorney, Agent, or Firm* — Fitzpatrick, Cella, Harper & Scinto

(57) ABSTRACT

An X-ray imaging apparatus is provided. The apparatus includes an X-ray sensor unit that detects X-rays, and a control unit that controls driving of an X-ray generator and the X-ray sensor unit. The control unit performs alignment imaging for imaging a still image of a subject. The still image is used as a reference for alignment of at least one of the X-ray generator and the X-ray sensor unit. After the alignment imaging, the control unit performs main imaging for imaging a moving image of the subject. The alignment imaging and the main imaging are performed under the same driving condition of the X-ray sensor unit.

14 Claims, 5 Drawing Sheets

(56) References Cited

U.S. PATENT DOCUMENTS

2010/0027752 A1* 2/2010 Matsumoto .................. 378/115
2011/0026676 A1* 2/2011 Takekoshi .................. 378/98.2
2011/0058727 A1    3/2011 Tsujii ........................ 382/132
2011/0216884 A1    9/2011 Tsujii et al. ................. 378/62

FOREIGN PATENT DOCUMENTS

| JP | 2002-305687 | 10/2002 |
| JP | 2004-144713 | 5/2004 |
| JP | 2009-119021 | 6/2009 |

* cited by examiner

X-RAY IMAGING APPARATUS

BACKGROUND OF THE INVENTION

1. Field of the Invention

The present invention relates to an X-ray imaging apparatus.

2. Description of the Related Art

In X-ray fluoroscopic radiography, sensor driving is switched between moving image driving during shooting and still image driving when displaying still images. In an apparatus in which alignment of an X-ray generator and an X-ray sensor unit is performed by an operator, usually, alignment imaging is performed with a still imaging mode and serial imaging is performed with a moving imaging mode.

For example, Japanese Patent Laid-Open No. 2002-305687 discloses a technology in which multiple bias power sources are provided and bias voltage applied to a sensor is switched between the moving image mode and the still image mode. Japanese Patent Laid-Open No. 2002-305687 describes that a preparation period is provided to refresh a sensor in advance before a radiography period in which the charge generated through photoelectric conversion after X-ray exposure is read out so as to obtain one still image.

Moreover, Japanese Patent Laid-Open No. 2009-119021 discloses the technology of performing auxiliary imaging in which a subject is serially imaged with a reduced amount of radiation irradiated before performing main still imaging of the subject. Japanese Patent Laid-Open No. 2009-119021 discloses detecting periodicity of movement of the subject based on images obtained by the auxiliary imaging, generating pseudo images based on the periodicity, and calculating imaging parameters to be used in main still imaging based on these pseudo images.

Japanese Patent Laid-Open No. 2004-144713 discloses the technology of changing settings of pixel density depending on whether still images or moving images are formed based on read images. Japanese Patent Laid-Open No. 2004-144713 discloses that when still images are formed it is preferable to perform high pixel density reading in order to obtain high resolution images, and that when moving images are formed it is preferable to perform rapid low pixel density reading in order to secure the frame rate required of moving images.

When sensor driving is switched between still imaging and moving imaging, the sensor becomes unstable and correction errors occur at the time of switching. Therefore, conventionally, at the time of switching, standby time is needed until the sensor becomes stable. However, this standby time impairs usability for the operator.

SUMMARY OF THE INVENTION

Therefore, the present invention provides an X-ray imaging apparatus that does not require standby time at the time of switching an imaging mode between still imaging and moving imaging and thereby improves usability for the operator.

According to one aspect of the present invention, an X-ray imaging apparatus includes an X-ray sensor unit configured to detect X-rays, and a control unit configured to control driving of the X-ray sensor unit, wherein the control unit performs alignment imaging for imaging a still image of a subject, the still image being used as a reference for alignment of the X-ray sensor unit, and the control unit performs main imaging for imaging a moving image of the subject after the alignment imaging, and wherein the alignment imaging and the main imaging are performed under a same driving condition of the X-ray sensor unit.

Further features of the present invention will become apparent from the following description of exemplary embodiments (with reference to the attached drawings).

DESCRIPTION OF THE EMBODIMENTS

Various exemplary embodiments, features, and aspects of the invention will be described in detail below with reference to the drawings.

Hereinafter, various exemplary embodiments of the present invention are described in detail with reference to the accompanying drawings. It should be noted that the following embodiments are not to be construed as limiting the invention, but as illustrating specific examples that are advantageous for the implementation of the present invention. In addition, all of the combinations of features that are described in the following embodiments are not necessarily essential to the problem solving means of the present invention.

Figure 1:
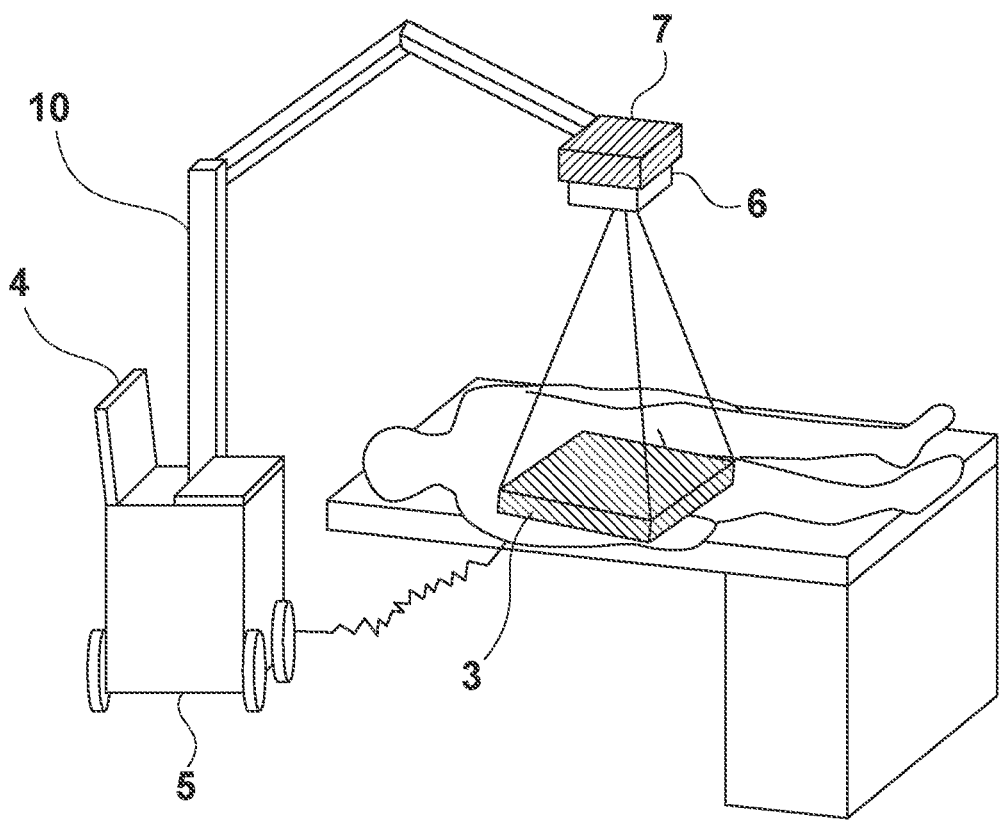
FIG. 1 is an external view of an X-ray imaging apparatus according to an embodiment.

FIG. 1 shows a general view of an X-ray apparatus according to an embodiment. X-rays generated in an X-ray generator 7 pass through an X-ray aperture unit 6, permeate the subject, reach an X-ray sensor unit 3, and then are detected by the X-ray sensor unit 3. Driving of the X-ray generator 7 and the X-ray sensor unit 3 is controlled by a control unit 5. An arm 10 extending from a case including the control unit 5 and an X-ray power source supports the X-ray generator 7. An X-ray image that has reached the X-ray sensor unit 3 undergoes image processing in the X-ray unit 5 and then is displayed on a display unit 4.

The operator is able to adjust the position of the arm 10 so that the X-ray beams can reach a plane of the X-ray sensor unit 3. Conventionally, such an X-ray apparatus has not been used for taking moving images. However, recent X-ray sensor units can take moving images even if they have a cassette configuration. In such a situation, before performing moving imaging, alignment of at least one of the X-ray generator 7 and the X-ray sensor unit 3 is required. In order to perform alignment, alignment imaging is needed to obtain still images of the subject used as the reference for alignment. Patients will be exposed to undesirable radiation if alignment operation is performed during moving imaging.

Figure 2:
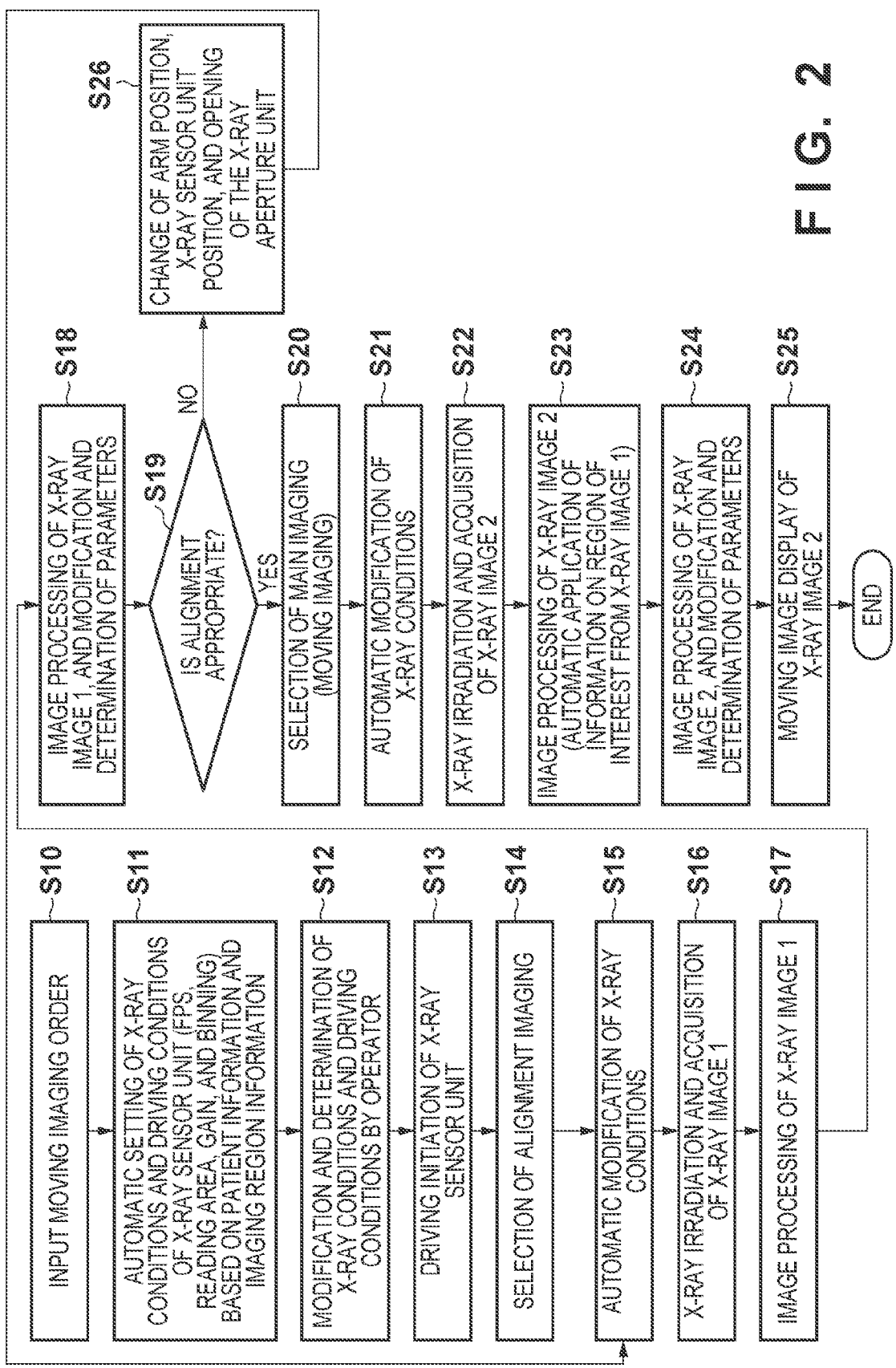
FIG. 2 is a flowchart of moving imaging by an X-ray imaging apparatus according to an embodiment.

FIG. 2 shows a flow of imaging according to the present embodiment. First, an order of moving imaging is input (S10). The order of moving imaging is carried out by computer communication with a radiology information system RIS (not shown), and thus patient information and imaging region information are attached to the order. Patient information includes disease information (types of disease) and information such as age, gender, body height, and body weight of a patient. Imaging region information includes information about such areas as the head, the lungs, the stomach, the pancreas, the bile duct, the liver, the small intestine, and the colon. It should be noted that imaging requiring high frame rates (fps), such as imaging of the heart, is not performed using such an X-ray imaging apparatus. It is assumed that the frame rate for taking moving images in the present embodiment is, for example, 5 fps or less.

X-ray conditions and driving conditions of the X-ray sensor unit 3 are automatically determined based on patient information and imaging region information (S11). X-ray conditions include, for example, tube voltage and mA values of X-ray pulses. Driving conditions of the X-ray sensor unit 3 include, for example, the frame rate (fps), reading area, gain and binning. The reading area means a whole area of a photo-receiving unit of the X-ray sensor unit 3 or a partial area of the photo-receiving unit of the X-ray sensor unit 3, in which case, the size of the area is expressed as a distance from the center of the sensor. The gain means a gain by an inner amplifier of a semiconductor sensor. Binning means how many pixels are combined to be read. For example, when the size of the original pixels are 160 μm×160 μm, the image size becomes 320 μm×320 μm if the original pixels are read by 2×2 pixels. For children, the tube voltage is set to low and the mA values of X-ray pulses are set to small. When the imaging region is the trunk of the body, the tube voltage is set to high, the mA values of X-ray pulses and the reading area are set to large, the gain is set to high, and the binning is set to large. The frame rate is determined based on disease information. The frame rate is set to high for the pulmonary region, which moves, and the frame rate is set to low for the head and abdominal region, which do not move much. It may be possible that X-ray conditions and driving conditions of the X-ray sensor unit 3 that are automatically set in S11 are modified and determined by the operator (S12).

Once the driving conditions of the X-ray sensor unit 3 are determined, driving of the X-ray sensor unit 3 is actually initiated (S13). The reason why the X-ray sensor unit 3 is not driven prior to the determination by the operator in S12 is to prevent power consumption by driving and an unnecessary temperature increase of the X-ray sensor unit 3.

Next, alignment imaging or main imaging (moving imaging) is selected by the operator (imaging mode selection). Generally, alignment imaging is needed prior to main imaging (S14). For alignment imaging, a smaller dose of radiation than a dose of radiation used for main imaging is sufficient. Since X-ray conditions determined in S12 are used in main imaging, X-ray conditions determined in S12 are automatically modified when alignment imaging is selected (S15). For example, a dose of radiation for alignment imaging is set to a predetermined ratio (for example, 10%-30%) of a main imaging dose. Alignment imaging is initiated by responding to the X-ray exposure instruction issued by an X-ray exposure button (not shown) being pressed, and then an X-ray pulse is emitted once. Since the X-ray sensor unit 3 has already been driven in S13, X-rays are emitted corresponding to the driving of the X-ray sensor unit 3, and an X-ray image 1 is acquired (S16). The present embodiment is different from conventional still imaging (alignment imaging) in that X-rays are emitted corresponding to the driving of the X-ray sensor unit 3.

The X-ray image 1 undergoes image processing in an image processing unit in the control unit 5 and then is displayed on the display unit 4 (S17). An alignment image displayed on the display unit 4 undergoes scaling to fit a predetermined size regardless of the driving conditions for moving images (binning and gain), and then is displayed on the display unit 4. Conventionally, alignment imaging is performed based on driving conditions for still images regardless of driving conditions of main imaging (moving imaging). The present invention is different from the conventional imaging in that alignment imaging is carried out based on driving conditions for moving images. Image processing parameters used in S17 are parameters that are determined through image processing, and such parameters may be modified and determined by the operator when they are not appropriate (S18).

The operator can judge whether or not alignment is appropriate based on observation of the X-ray image 1 that has undergone modification image processing (S19). When the alignment is not appropriate, the arm position, the position of the X-ray sensor unit 3, and the opening of the X-ray aperture unit 6 are modified as needed (S26). After modifications, the procedure goes to S15. In this case, in S15, graininess of alignment images is automatically judged, and then X-ray conditions are automatically modified. The alignment images may not particularly require good image graininess, and thus when the image graininess is better than the requirement, mA values of the X-ray pulses are modified to be small.

When the alignment is appropriate, main imaging (moving imaging) is then selected (S20). The values that are modified to be small for alignment imaging in S15 such as mA values of the X-ray conditions revert to the X-ray conditions determined in S12 (S21). Main imaging is initiated by responding to the X-ray exposure instruction issued by the X-ray exposure button (not shown) being pressed, and then an X-ray pulse is emitted continuously more than once. The number of X-ray pulses, for example, can be calculated by multiplying the number of seconds the X-ray exposure button is pressed by the fps of driving conditions of the X-ray sensor unit 3. The X-ray pulse is output corresponding to the X-ray sensor unit 3, and an X-ray image 2 is acquired (S22).

Figure 5:
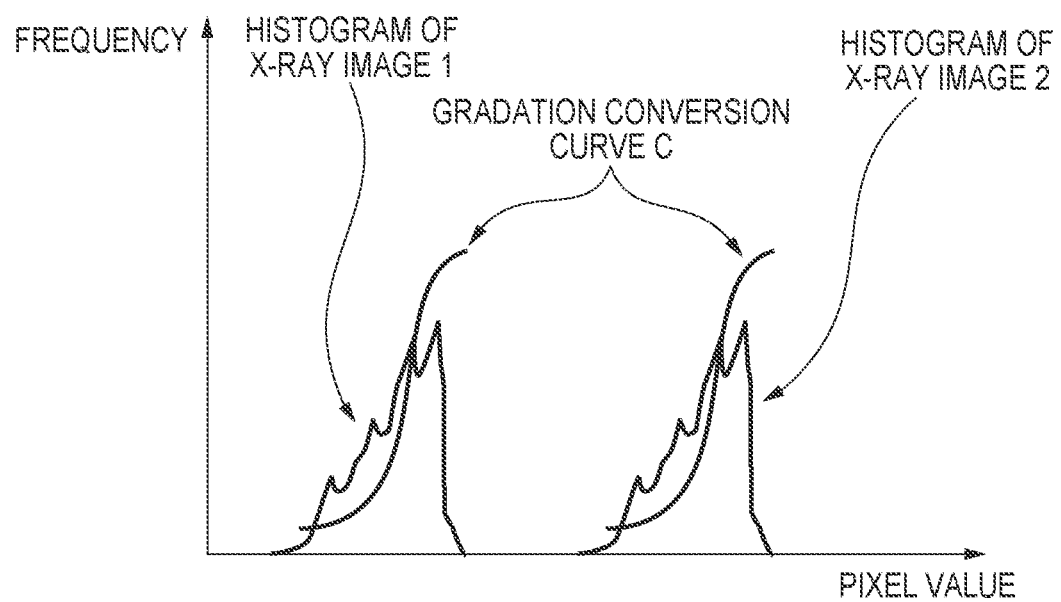
FIG. 5 is a graph showing gradation conversion according to an embodiment.

Information on the region of interest determined in S18 is applied to the X-ray image 2, and then the X-ray image 2 undergoes image processing and is continuously displayed on the display unit 4 (S23). Since the X-ray dose differs between the X-ray image 1 and the X-ray image 2, the graininess of images and pixel values differ between these images. Thus, proper images cannot be obtained through the same frequency enhancement or the same gradation conversion. However, since an imaging region of the subject is the same, the region of interest is also the same. When gradation conversion is carried out, the settings of the region of interest is important. The information on the region of interest can be designated by the positional relation between pixel value histograms of X-ray images and gradation conversion curves. A position on the pixel value histogram of the X-ray image 1 on the gradation conversion curve C determined in S18 is stored, and the position is set to the same position as the position on the pixel value histogram of the X-ray image 2 and on the gradation conversion curve C. The gradation conversion curve C applied to the X-ray image 1 and the X-ray image 2 is identical (FIG. 5). Image processing parameters applied in S23, excepting for gradation conversion, are parameters that are determined through image analysis, and such parameters may be modified and determined by the operator when they are not appropriate (S24). The X-ray image 2 is continuously displayed based on the image processing parameters determined in S24 (S25).

As mentioned above, in the present embodiment, the driving conditions of the X-ray sensor unit 3 are shared for alignment imaging and main imaging.

Figure 3:
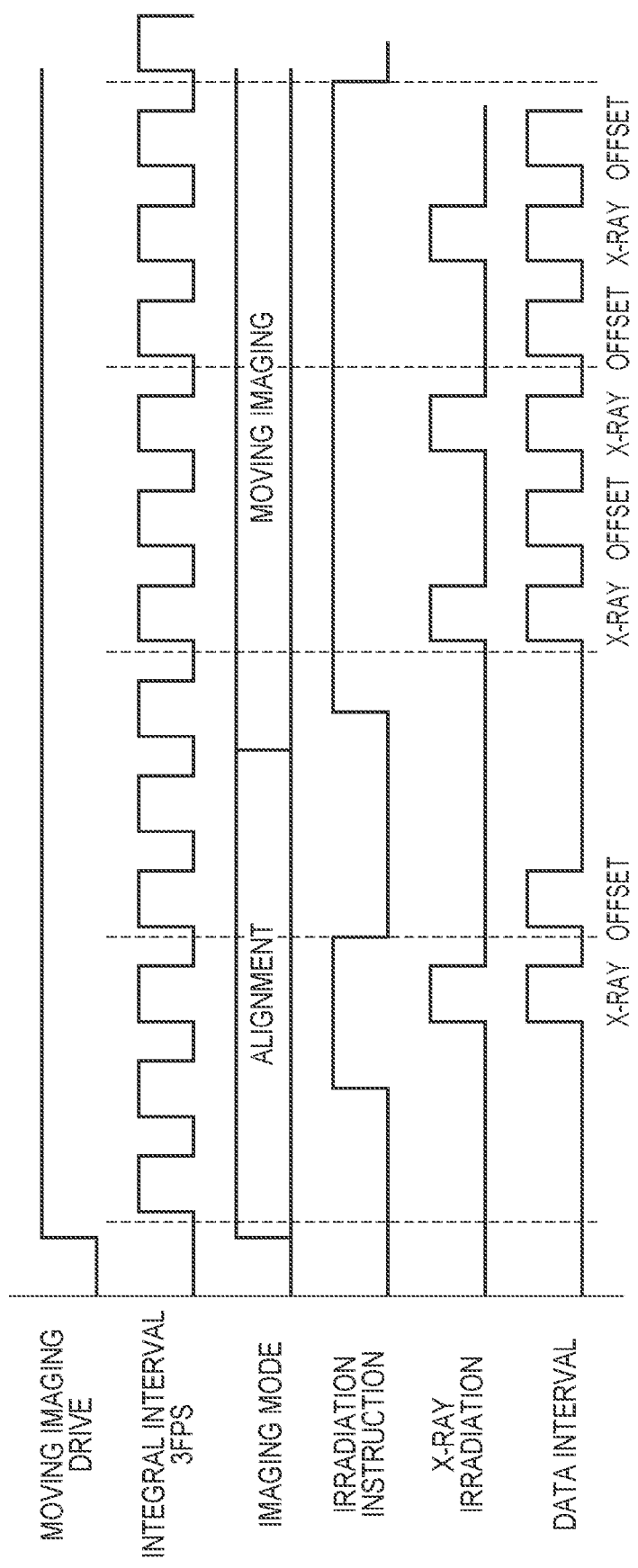
FIG. 3 is a timing chart showing an example of driving of an X-ray sensor unit according to an embodiment.

Hereinafter, a method for acquiring X-ray images is described when both alignment imaging and main imaging are performed based on driving conditions (the frame rate (fps), gain, reading area, and binning) of main imaging. FIG. 3 is a timing chart in the case where the X-ray sensor unit 3 is driven at a frame rate of 3 fps (three integral intervals in one second). In the present embodiment, half of the frame rate serves as an image display rate. When the driving conditions of the X-ray sensor unit 3 are determined in S13, a driving signal for moving imaging becomes active (becomes high). When the driving signal for moving imaging becomes active, the integral interval of the X-ray sensor unit 3 is determined as 3 fps. When alignment imaging is selected in the imaging mode selection of S14 and an exposure button (not shown) is pressed, an irradiation instruction signal becomes active for a given period of time (becomes high) regardless of a pressing period. X-rays are irradiated by logical conjunction (AND) of this irradiation instruction signal and the integral interval. X-ray signals (main signals) are acquired during the integral intervals during which the X-ray irradiation is performed. When X-rays are irradiated, OFFSET signals (dark current signal) are acquired during the subsequent integral intervals. An X-ray image is a difference between the X-ray signal and the OFFSET signal.

The X-ray image is displayed on the display unit 4 after image processing. At the time of the alignment imaging mode, integration is actually carried out during integral intervals that do not correspond to the irradiation instruction signal, and the X-ray sensor unit 3 is driven. However, an amplifier circuit and an AD converter circuit, which consume electric power, are not driven and thus image data are not generated.

When alignment imaging is performed again in S19, the irradiation instruction signal is output again corresponding to the exposure button being pressed. When the alignment is satisfactory in S19, the moving imaging is selected in the imaging mode selection, and when the exposure button (not shown) is pressed, the irradiation instruction signal is output, corresponding to the pressing period. X-rays are irradiated by logical conjunction (AND) of this irradiation instruction signal and the integral interval. However, X-rays are irradiated only for odd-numbered integral intervals. X-ray signals (main signals) are acquired during the integral intervals during which the X-ray irradiation is performed. When X-rays are irradiated, OFFSET signals (dark current signals) are acquired during the subsequent integral intervals. The X-ray image is a difference between the X-ray signal and the OFFSET signal. The X-ray image is displayed on the display unit 4 after image processing. In the present embodiment, the X-ray signal (main signal) is acquired and then the OFFSET signal is acquired. However, when the OFFSET signal is stable, instead of acquiring every OFFSET signal, a representative OFFSET signal acquired prior to the moving imaging can be used for all of the X-ray signals.

Figure 4:
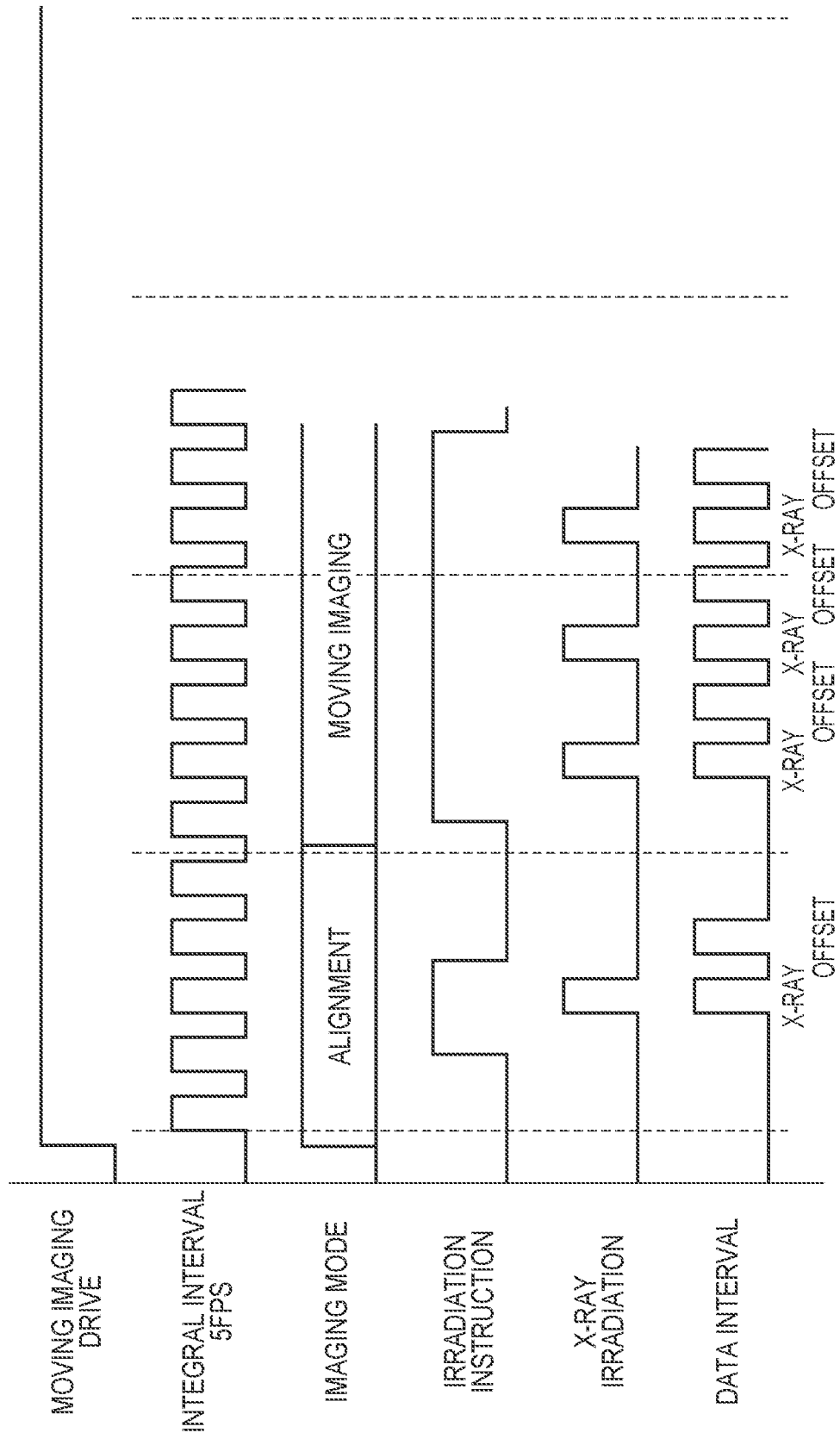
FIG. 4 is a timing chart showing an example of driving of an X-ray sensor unit according to an embodiment.

FIG. 4 is a timing chart in the case where the X-ray sensor unit 3 is driven at a frame rate of 5 fps (five integral intervals in one second). FIG. 4 is different from FIG. 3 in that the integral interval of the X-ray sensor unit 3 is short because five integral intervals are set to one second. When the imaging mode is set to the moving imaging, generally, the integral intervals vary depending on the frame rate. The present embodiment is different from the conventional technology in that the integral intervals vary also when the imaging mode is set to alignment (still) imaging. When the integral interval is shortened, a tube current value is needed to increase in order to add the same dose (mA value), but it is advantageous that alignment imaging can be rapidly switched to the moving imaging.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-144550, filed Jun. 29, 2011, which is hereby incorporated by reference herein in its entirety.

What is claimed is:

1. An X-ray imaging apparatus comprising:
   an X-ray sensor unit configured to detect X-rays; and
   a control unit configured to control driving of the X-ray sensor unit,
   wherein the control unit performs alignment imaging for imaging a still image of a subject, the still image being used as a reference for alignment of the X-ray sensor unit, and the control unit performs main imaging for imaging a moving image of the subject after the alignment imaging, and
   wherein the alignment imaging and the main imaging are performed under a same driving condition of the X-ray sensor unit.

2. The X-ray imaging apparatus according to claim 1, wherein the driving condition of the X-ray sensor unit includes frame rates, gains, and binning.

3. The X-ray imaging apparatus according to claim 1, wherein the control unit controls an X-ray generator so that an X-ray pulse is emitted once in response to an X-ray exposure instruction at the time of the alignment imaging, and the control unit controls the X-ray generator so that an X-ray pulse is emitted continuously more than once in response to an X-ray exposure instruction at the time of the main imaging.

4. The X-ray imaging apparatus according to claim 1, further comprising:
   a display unit configured to display a taken image,
   wherein the control unit performs scaling for the still image taken by the alignment imaging so that the still image fits a predetermined size regardless of the driving condition of the X-ray sensor unit, and then displays the still image on the display unit.

5. The X-ray imaging apparatus according to claim 1, wherein a frame rate of a moving image taken in the main imaging is 5 fps or less.

6. The X-ray imaging apparatus according to claim 1, further comprising:
   a setting unit configured to set an X-ray condition of an X-ray generator and a driving condition of the X-ray sensor unit based on patient information and imaging region information attached to an inputted order of moving imaging,
   wherein when the alignment imaging is performed the control unit modifies the X-ray condition set by the setting unit so that a dose of the alignment imaging corresponds to a predetermined ratio of a dose of the main imaging, and then when the main imaging is performed the control unit allows the modified X-ray condition to revert to the X-ray condition set by the setting unit.

7. An X-ray imaging apparatus comprising:
an X-ray sensor unit configured to detect X-rays to obtain an X-ray image; and
an imaging control unit configured to execute still imaging for imaging an X-ray image in response to a first operation, and to execute moving imaging for continuously imaging a plurality of frames of X-ray images in response to a second operation,
wherein the imaging control unit executes the still imaging and the moving imaging under the same driving condition of the X-ray sensor unit.

8. The X-ray imaging apparatus according to claim 7, further comprising a generation control unit configured to control a generation of the X-rays,
wherein the generation control unit controls the generation of the X-rays so as to generate the X-rays under different generation conditions depending on the still imaging and the moving imaging.

9. The X-ray imaging apparatus according to claim 7, wherein the imaging control unit sequentially-executes the still imaging and the moving imaging in response to the first and second operations.

10. The X-ray imaging apparatus according to claim 7, wherein the driving condition of the X-ray sensor unit includes a gain and a binning.

11. The X-ray imaging apparatus according to claim 7, wherein the control unit controls an X-ray generator so that an X-ray pulse is emitted once in response to an X-ray exposure instruction at the time of the still imaging, and the control unit controls the X-ray generator so that an X-ray pulse is emitted continuously more than once in response to an X-ray exposure instruction at the time of the moving imaging.

12. The X-ray imaging apparatus according to claim 7, further comprising a display unit configured to display a captured image,
wherein the control unit performs scaling for the still image captured by the still imaging so that the still image fits a predetermined size regardless of the driving condition of the X-ray sensor unit, and then displays the still image on the display unit.

13. The X-ray imaging apparatus according to claim 7, wherein a frame rate of the moving image captured in the moving imaging is 5 fps or less.

14. The X-ray imaging apparatus according to claim 7, further comprising:
a setting unit configured to set an X-ray condition of an X-ray generator and a driving condition of the X-ray sensor unit based on patient information and imaging region information attached to an inputted order of moving imaging,
wherein when the still imaging is performed, the control unit modifies the X-ray condition set by the setting unit so that a dose of the still imaging corresponds to a predetermined ratio of a dose of the moving imaging, and then when the moving imaging is performed, the control unit allows the modified X-ray condition to revert to the X-ray condition set by the setting unit.

* * * * *